(12) United States Patent
Kong et al.

(10) Patent No.: US 6,842,234 B2
(45) Date of Patent: Jan. 11, 2005

(54) APPARATUS FOR MEASURING SOOT CONTENT IN DIESEL ENGINE OIL IN REAL TIME

(75) Inventors: Hosung Kong, Seoul (KR); Hung-Gu Han, Seoul (KR); Eui-Sung Yoon, Seoul (KR); Lyubov Vasilievna Markova, Gomel (BY); Mikhail Savich Semenyuk, Gomel (BY)

(73) Assignee: Korean Institute of Science and Technology, Seoul (KR)

( * ) Notice: Subject to any disclaimer, the term of this patent is extended or adjusted under 35 U.S.C. 154(b) by 106 days.

(21) Appl. No.: 10/291,113

(22) Filed: Nov. 8, 2002

(65) Prior Publication Data

US 2004/0021849 A1 Feb. 5, 2004

(30) Foreign Application Priority Data

Aug. 2, 2002 (KR) ........................................ 2002-45777

(51) Int. Cl.[7] .............................................. G01N 33/28
(52) U.S. Cl. ......................................................... 356/70
(58) Field of Search ............................................ 356/70

(56) References Cited

U.S. PATENT DOCUMENTS 5,548,393 A * 8/1996 Nozawa et al. ................ 356/70
6,016,191 A * 1/2000 Ramos et al. .................. 356/70

* cited by examiner

Primary Examiner—Gregory J. Toatley, Jr.
Assistant Examiner—Amanda Merlino
(74) Attorney, Agent, or Firm—Jones Day

(57) ABSTRACT

An apparatus for measuring soot content in diesel engine oil in real time comprises an optical rod capable of transmitting light and having a boundary surface adapted to be in contact with the diesel engine oil and first and second end portions, a light-emitting portion, and a first optical fiber connected to the light-emitting means. The first optical fiber is adapted to transmit light from the light-emitting means to the first end portion of the optical rod in an aperture angle of the optical fiber to the boundary surface. The apparatus also comprises a light-receiving portion adapted to receive light from the optical rod and output a signal corresponding to the received light power. The refractive index of the optical rod is larger than the refractive index of the diesel engine oil. The aperture angle of the optical fiber is equal to or larger than a critical angle reduced to air at which the light is totally reflected by the boundary surface.

6 Claims, 6 Drawing Sheets

Concentration of Carbon Black Particles, weight ratio (%)

APPARATUS FOR MEASURING SOOT CONTENT IN DIESEL ENGINE OIL IN REAL TIME

FIELD OF THE INVENTION

The present invention relates to an apparatus for measuring soot content in oil, and particularly to an apparatus for measuring soot content in diesel engine oil in real time by detecting a change of light power passing through an optical rod immersed in the oil, which is reflected by a boundary surface of the optical rod in contact with the oil containing carbon soots.

BACKGROUND OF THE INVENTION

Generally, the lifespan of engine oil depends on a running distance of a vehicle or operating time of the engine. As time passes, engine oil is oxidized or nitrified, and deteriorates by being mixed with carbon soots, metallic particles, fuel oil or coolant. Various apparatus for detecting engine oil deterioration are required, which are usually costly for both manufacturers and consumers. There is a need for a primary apparatus for detecting oil deterioration in an effective manner. When detecting diesel engine oil deterioration, measurement of carbon soot content in oil is most preferable.

Diesel fuel is mostly burned in a combustion chamber. A portion of the fuel is unburned and subject to thermal decomposition under high temperature. Unburned fuel components generate carbon soot particles. A portion of the carbon particles is discharged to the atmosphere by exhaust fumes, and the portion remaining in the combustion chamber is mixed with engine oil. Carbon particles in the engine oil are transformed into soot lumps by reacting with engine additives such as dispersing agent or detergent. The soot lumps reduce flow rate of the engine oil by increasing its viscosity, and cause excessive wear on the surfaces of engine components like cylinders, bearings, and the like, thereby deteriorating engine performance considerably. Accordingly, the oil change maintenance period depends largely on the carbon soot content.

Allowable carbon soot content in diesel engine oil is in the range of about 0.5% to 4%. Carbon soot generated in a diesel engine is a very minute spherical particle ranging from several tens of nanometers to dozens of micrometers, and is impossible to filter with conventional oil filters.

Several apparatus for measuring quantitative carbon soot content in oil are known, and a thermal gravimetric analyzer is most widely used. As a thermal gravimetric analyzer is used to test small amounts of sample oil extracted from the engine, it is incapable of measuring oil contamination in real time.

The state of the art apparatus for measuring carbon soot content in real time measures variation of dielectric constant of the oil.

An example of an apparatus for measuring soot content using variation of dielectric constant of oil is the fluid condition monitor disclosed in U.S. Pat. No. 6,278,281 issued to Bauer et al. The method of monitoring fluid condition comprises the steps of immersing a pair of electrodes in the fluid; applying an oscillating, substantially constant peak supply voltage sequentially at a first frequency of at least one hertz and at a second frequency of less than one hertz across the electrodes; measuring the current at the first frequency representative of the bulk impedance of the fluid and the second frequency representative of the surface impedance of the electrodes, and calculating the difference of the measured currents; and comparing the difference in measured currents with a reference level for a predetermined acceptable fluid condition.

The apparatus of U.S. Pat. No. 6,278,281 which uses variation of dielectric constant in oil, reacts very sensitively to oil oxidization, water, metallic wear particles mixed with the oil as well as the concentration of carbon particles. This apparatus, therefore, cannot accurately measure the carbon soot content in oil. Additionally, the apparatus cannot monitor oil condition accurately since it is sensitive to electrical disturbances and dependent on temperature, which are common problems with most apparatus depending on electric characteristics of the oil.

Examples of apparatus for measuring oil contamination with emitted light in oil are described in U.S. Pat. No. 4,699,509 issued to Kamiya et al., and U.S. Pat. No. 5,548,393 issued to Nozawa et al.

U.S. Pat. No. 4,699,509 discloses a device for measuring contamination of lubricant, in which an optical path gap is provided between a light source window at a light source side and a light receiving window at a light receiving element side. A lubricant having an amount of contaminant to be measured in accordance with light transmittance is present in the optical path gap, and the length of the optical path gap is dozens of micrometers.

It is difficult for lubricant to flow smoothly through such a short optical path gap because of flow resistance due to viscosity of the lubricant, and the length of the optical path gap must be adjusted accurately and maintained constant.

The oil deterioration detecting apparatus of U.S. Pat. No. 5,548,393 applies the "Goos-Hänchen shift" phenomenon. When light advances from a first medium with a first refractive index to a second medium with a second refractive index at an angle larger than a total reflection critical angle, the light will not enter the second medium with the second refractive index, and will be totally reflected. The reflection light goes out from a point apart from an incidence point by a certain distance, and the distance is called "Goos-Hänchen shift."

The apparatus of U.S. Pat. No. 5,548,393 comprises a prism having a boundary surface in contact with the liquid to be examined; a light-emitting portion for emitting light toward the boundary surface; and a photosensor for receiving the light reflected by the boundary surface with "Goos-Hänchen shift" and for outputting a signal corresponding to the amount of the received light. The light power changes in accordance with the concentration of carbon particles in the oil.

In the apparatus of U.S. Pat. No. 5,548,393, the boundary surface in contact with the liquid to be examined is limited to one or three, and precise measurement can not be achieved for low level of contamination. Also, this prior art apparatus ignores the possibility that refractive index of the liquid may increase as the soot content in the liquid increases. In other words, when the soot content in the liquid increases, the critical angle at which the light is totally reflected by the boundary surface, also increases more than when the liquid is clean. Therefore, the incidence angle of light becomes smaller than the critical angle, thereby violating the total reflection condition. Accordingly, the power of light reflected by the boundary surface decreases considerably, and the oil deterioration is exaggerated and erroneously detected as if the soot content in the oil were very high.

Furthermore, the above prior art apparatus further comprises additional complicated components such as ball-shaped cleaning members disposed in the liquid which are moved throughout the liquid and contact the boundary surface, and flow-out prevention members adapted to prevent the cleaning members from flowing away from a location near the boundary surface. Because the contaminant adheres to the surfaces of the cleaning members as well as the boundary surface in the diesel engine oil having a high soot content, the cleaning effect by the members is very small. And, further problems are introduced when the contaminated cleaning members have to be replaced with fresh members. It is difficult to determine the appropriate exchange times for such cleaning members.

SUMMARY OF THE INVENTION

It is an object of the present invention to provide an apparatus for measuring soot content in diesel engine oil in real time by detecting a change of light power of passing through an optical rod immersed in diesel engine oil, which is reflected by a boundary surface of the optical rod in contact with oil containing carbon soots.

In order to achieve the above object, the present invention provides an apparatus for measuring soot content in diesel engine oil in real time comprising an optical rod which is capable of transmitting light, and has a boundary surface adapted to be in contact with the diesel engine oil, and a first end portion and a second end portion. The apparatus also comprises a light-emitting means, and a first optical fiber connected to the light-emitting means. The first optical fiber is adapted to transmit light from the light-emitting means to the first end portion of the optical rod in an aperture angle of the optical fiber to the boundary surface. The apparatus also comprises a light-receiving means adapted to receive light from the optical rod and output a signal corresponding to the received light power.

The refractive index of the optical rod is larger than the refractive index of the diesel engine oil, and the aperture angle of the optical fiber is equal to or larger than a critical angle reduced to air at which the light is totally reflected by the boundary surface.

The optical rod is of a cylindrical shape and a transparent material with a predetermined length and diameter. Preferably, the ratio of length to diameter of the optical rod is at least 10:1. The boundary surface is a longitudinal outer peripheral surface of the optical rod.

A hydrophobic material for preventing adherence of contaminants is coated onto the boundary surface. The refractive index of the hydrophobic material should be equal to or less than the refractive index of the optical rod, and larger than the refractive index of the diesel engine oil. Preferably, the hydrophobic material is octadecyltrichlorosilane.

The inventive apparatus further comprises at least one second optical fiber which is connected to the light-receiving means and extends toward the first end portion of the optical rod. A mirror is provided at the second end portion of the optical rod and reflects light emitted from the first optical fiber and passed through the optical rod toward the at least one second optical fiber. The second optical fiber is adapted to surround the first optical fiber. A housing has a plurality of perforations, and houses the optical rod.

A temperature detecting member is mounted in the housing and electrically connected to a microprocessor. The microprocessor activates the light-emitting means and the light-receiving means when the diesel engine oil rises to a preset temperature based on signals from the temperature detecting member.

BRIEF DESCRIPTION OF DRAWINGS

The above object and features of the present invention will become more apparent from the following description of the preferred embodiments given in conjunction with the accompanying drawings.

DETAILED DESCRIPTION OF THE PRESENT INVENTION

Preferred embodiments of the present invention will now be described with reference to the accompanying drawings.

Figure 1:
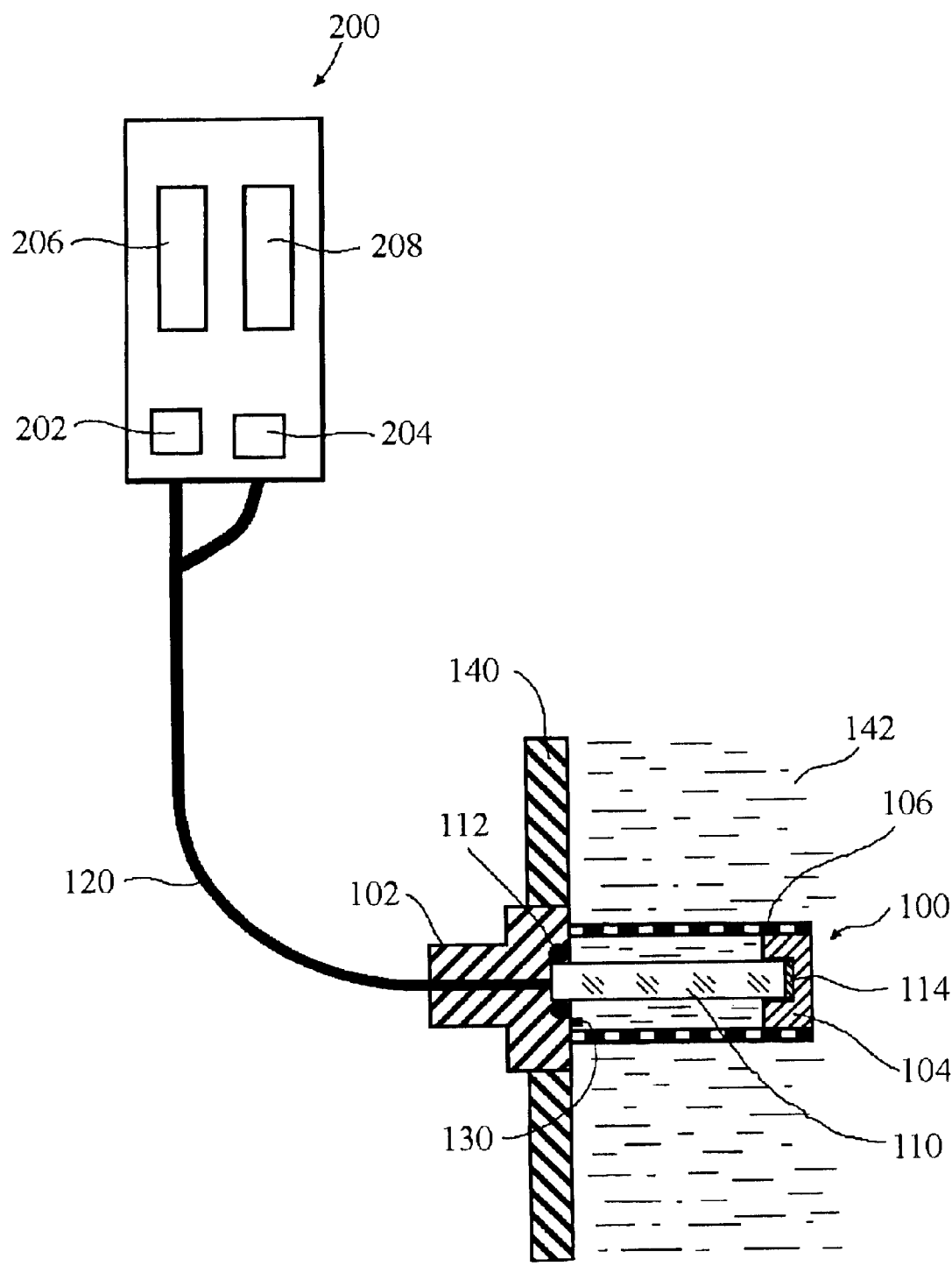
FIG. 1 shows an apparatus for measuring soot content in diesel engine oil in real time in accordance with a preferred embodiment of the present invention.
Figure 2:
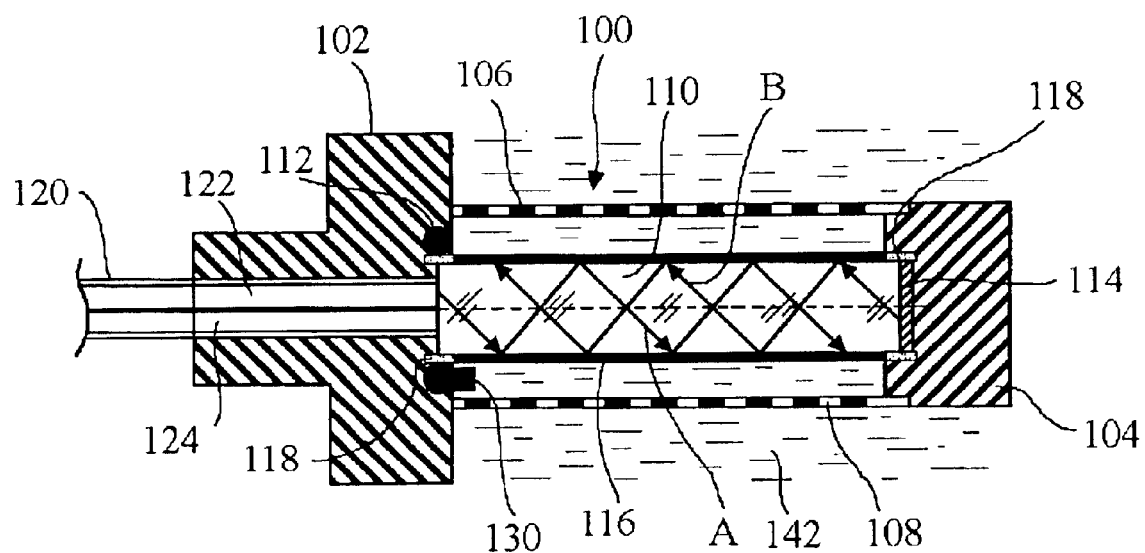
FIG. 2 is a sectional view depicting a sensing portion and a light transmission portion of the apparatus shown in FIG. 1.

FIG. 1 shows an apparatus for measuring soot content in diesel engine oil in real time in accordance with a preferred embodiment of the present invention, and FIG. 2 is a sectional view showing a sensing portion and a light transmission portion of the apparatus depicted in FIG. 1.

As shown in the drawings, the inventive apparatus for measuring soot content in diesel engine oil in real time comprises a sensing portion 100 which is mounted in a container 140 storing diesel engine oil 142, a signal processing portion 200 which processes a signal corresponding to the light passing through the sensing portion 100, and a light transmission portion 120 which transmits the light between the sensing portion 100 and the signal processing portion 200.

The signal processing portion 200 includes a light-emitting portion 202 which emits the light toward the sensing portion 100, a light-receiving portion 204 which receives the light passing through the sensing portion 100 and outputs a signal corresponding to the received light, and a display portion 206 which displays the output signal from the light-receiving portion 204.

The sensing portion 100 includes a first supporting member 102 which is fixed to a wall of the oil container 140, a hollow housing 106 which is formed with a plurality of minute perforations 108 and a first end of which is fixed to the first supporting member 102, a second supporting member 104 to which a second end of the housing 106 is fixed, and an optical rod 110 which is disposed in a space defined by the supporting members 102 and 104 and the housing 106 to be immersed in the diesel engine oil 142 and has a boundary surface in contact with the oil 142.

The light transmission portion 120 has first and second optical fibers 122 and 124 which are connected to the light-emitting and light-receiving portions 202 and 204, respectively, and extend adjacent to a first end of the optical rod 110.

The signal processing portion 200 is spaced apart from the oil container 140 by a certain distance by the optical fibers 122 and 124, so that the electric noise can be reduced.

The cylindrical optical rod 110 has a predetermined length and diameter, and is made from a transparent material such as glass through which the light can pass. Both ends of the optical rod 110 are fixed to the supporting members 102 and 104. The longitudinal outer periphery surface of the optical rod 110 is the boundary surface in contact with the engine oil 142.

The housing 106, the optical rod 110 and the second supporting member 104 are located inside the oil container 140 while being immersed in the oil 142. The oil 142 flows into the housing 106 through the perforations 108 of the housing 106, so that the oil 142 contacts the outer periphery surface, i.e., the boundary surface, of the optical rod 110.

The perforations 108 of the housing 106 prevent large foreign substances which are irrelevant to the measurement of the oil contamination from entering the housing 106 and contacting the optical rod 110. In addition, air bubbles existing in the oil 142 are dispersed by going through the perforations 102, so as not to influence the measurement of the oil contamination.

An O-ring 112 is mounted between the first supporting member 102 and the optical rod 110 to prevent the leakage of the oil 142.

A second end of the optical rod 110, opposite to the light transmission portion 120, is provided with a mirror 114 for reflecting the light. The light emitted from the light-emitting portion 202 is transmitted to the first end of the optical rod 110 via the first optical fiber 122 with aperture angle in the direction of optical axis of the optical rod 110, and progresses toward the boundary surface in contact with the oil 142. As directed by arrow A depicted in FIG. 2, the light is totally reflected several times by the boundary surface, until the light reaches the mirror 114 and is reflected thereby. Then, as directed by arrow B depicted in FIG. 2, the light is totally reflected several times by the boundary surface and transmitted to the light-receiving portion 204 via the second optical fiber 124.

A thermister 130 for detecting a change of oil temperature is mounted in the housing 106, and electrically connected to a microprocessor 208 mounted to the signal processing portion 200. When the oil temperature is determined to rise to a pre-determined value, e.g., 80° C., by the thermister 130, the microprocessor 208 operates the inventive apparatus to measure oil contamination. Generally, because variation of refractive index of the diesel engine oil is relatively larger under the oil temperature of 80° C. or less, the light refraction and total reflection characteristics in the optical rod 110 are influenced, so the accurate measurement of oil contamination can not be achieved. But, since the temperature of diesel engine oil reaches 80° C. right after starting engine, it is not a serious problem that the oil contamination can not be measured during an initial engine operation.

A hydrophobic material 116 is coated on the outer surface of the optical rod 110 to prevent contaminants from sticking thereto. The refractive index of the coated hydrophobic material 116 is equal to or smaller than that of the optical rod 110, and larger than that of the oil 142, in order not to violate the total reflection condition, which will be described later, at the boundary surface of the optical rod 110 in contact with the oil 142.

For example, if the refractive indexes of the optical rod 110 and the oil 142 are 1.55 and 1.52, respectively, the refractive index of the hydrophobic material 116 is in the range of 1.53 to 1.55. Preferably, octadecyltrichlorosilane can be applied as the hydrophobic material 116.

Another material 118 may be coated on the surface of the optical rod 110 contacting the O-ring 112 and the supporting members 102 and 104 for preventing optical radiation loss at the contacting surface. The refractive index of the material 118 is smaller than that of the optical rod 110. For example, if the refractive index of the optical rod 110 is 1.55, the material 118 having the refractive index ranging from 1.45 to 1.50 is coated.

Figure 3A:
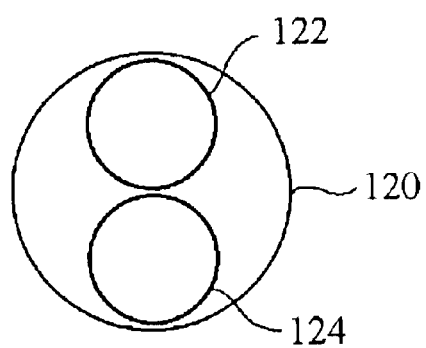
FIG. 3a is a sectional view showing a first embodiment of the light transmission portion.
Figure 3B:
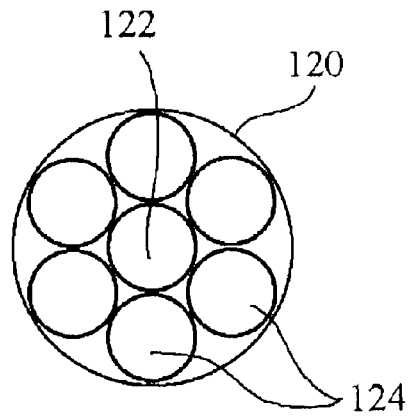
FIG. 3b is a sectional view showing a second embodiment of the light transmission portion.

FIGS. 3a and 3b are sectional views showing preferred embodiments of the light transmission portion 120.

As shown in FIG. 3a, the first optical fiber 122 connected to the light-emitting portion 202 and the second optical fiber 124 connected to the light-receiving portion 204 are provided by one for each. On the other hand, as shown in FIG. 3b, the first optical fiber 122 is provided by one, and a plurality of second optical fibers 124 are provided while surrounding the first optical fiber 122.

If a plurality of second optical fibers 124 are provided, the larger amount of the light passing through the optical rod 110 is transmitted to the light-receiving portion 204 via the second optical fibers 124, thereby achieving a higher optical output in comparison with one additional second optical fiber.

Hereinafter, a principle of measuring soot content in diesel engine oil by using the apparatus in accordance with the present invention will be described.

Generally, a refractive index of oil is expressed as $\bar{n}=n-in'$. Here, n is a real part, and n' is an imaginary part.

The real part n of the refractive index is determined by a phase lag of a wave going through a medium, and changed in accordance with oil oxidization, inflow of fuel oil and coolant, or contamination due to soot particles. The imaginary part n' means an absorption index value, and is determined by the amount of light absorbed by the soot particles.

In other words, the measuring principle of the inventive apparatus is based upon the physical phenomenon of that the complex refractive index $\bar{n}$ of the oil 142 is changed in accordance with the concentration of the carbon particles in the oil 142 and accordingly the light power is changed after the light passes through the optical rod 110 immersed in the oil 142 while being reflected by the boundary surface in contact with the oil 142.

When the light goes from a first medium to a second medium which have different refractive indexes, the light is totally reflected by the boundary surface therebetween, if an incidence angle $\theta_1$ is equal to or more than a total reflection critical angle $\theta_{cr}$, as described by the following equation (1).

$$\theta_1 \geq \theta_{cr} = \arcsin\left(\frac{n_2}{n_1}\right) \qquad \text{Eq. (1)}$$

Here, $n_1$ and $n_2$ are refractive indexes of the first and second media, respectively.

If an optical loss does not exist in the first medium or is so small as to be disregarded, a certain amount of light is absorbed in the second medium in accordance with a light-absorbing element therein, e.g., carbon soots in diesel engine oil, and the power of light reflected by the boundary surface is reduced, thereby measuring quantitatively soot content in diesel engine oil.

In the present invention, the refractive index of the optical rod 110 is set to be larger than that of the diesel engine oil 142, and thus the light passing through the optical rod 110 is induced to be totally reflected by the boundary surface.

However, since the amount of light absorbed by soots in the oil 142 is very small, if the reflection by the boundary surface occurs only one time, it is difficult to acquire an enough changed value of light to measure oil contamination. So, it is necessary to accumulate the light decrement effect by generating several reflections by the boundary surface and obtain relatively large changed value of light power.

Figure 4:
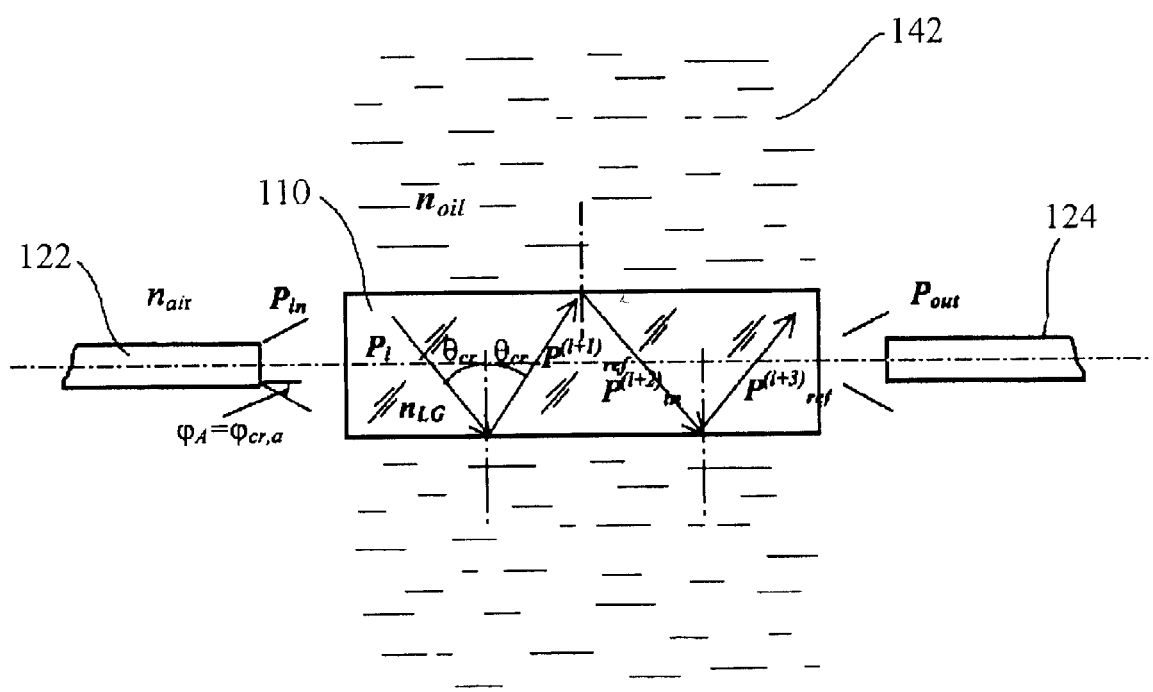
FIG. 4 depicts an optical rod through which light passes while being totally reflected by a boundary surface in contact with diesel engine oil.

The principle of measuring soot content in diesel engine oil by using the inventive apparatus will be described more in detail with reference to FIG. 4.

The light transmitted to the optical rod 110 via the optical fiber 122 with aperture angle $\phi_A$ in the direction of optical axis of the optical rod 110 progresses while being totally reflected several times by the boundary surface in contact with the oil 142.

The power $P_{out}$ of the light passing through the optical rod 110 and transmitted to the optical fiber 124 is described by the following equation (2).

$$P_{out} = \int_{\varphi=-\varphi_{cr,a}}^{\varphi=+\varphi_{cr,a}} P_{in}(\varphi) \cdot R_{TIR}^m(\varphi, \bar{n}_{oil}) d\varphi \qquad \text{Eq. (2)}$$

$P_{in}(\phi)$ means a power of light radiated to the optical rod 110 from the optical fiber 122, $\phi$ is an incidence angle of light into the optical rod 110, $\phi_{cr,a}$ refers to a critical angle at which the light entering the optical rod 110 from the air is totally reflected by the boundary surface in contact with the diesel engine oil 142, and m is a number of times of that the light is totally reflected by the boundary surface when the light passes through the optical rod 110.

The total reflection critical angle $\phi_{cr,a}$ depends upon the real part $n_{oil}$ of the refractive index of the oil 142. On the other hand, $R_{TIR}(\phi, \bar{n}_{oil})$ is a reflection coefficient, which has a value near 1 if no light-absorbing element exists in the oil 142 and has a value smaller than 1 if a light-absorbing element exists. The relation between the reflection coefficient and refractive index of the oil 142 having a light-absorbing element can be described by the following equation (3), which applies the Fresnel's formula.

$$R(\varphi, \bar{n}_{oil}) = 1 - \frac{4 \cdot n_{oil} \cdot \sin\varphi}{(n_{LG}^2 - n_{oil}^2)(n_{LG}^2 - n_{oil}^2 - \sin^2\varphi)^{\frac{1}{2}}} n'_{oil} \qquad \text{Eq. (3)}$$

$n_{LG}$ means a refractive index of the optical rod 110.

In other words, when the real part of the refractive index is constant and the diesel engine oil is contaminated with carbon soots, the reflection coefficient $R(\phi, \bar{n}_{oil})$ is primarily dependent upon the absorption index $n'_{oil}$ of the oil 142. Accordingly, the $P_{out}$ of light outputted from the optical rod 110 after being reflected several times by the boundary surface of the optical rod 110 decreases in proportion to the soot content in the oil 142.

Figure 5:
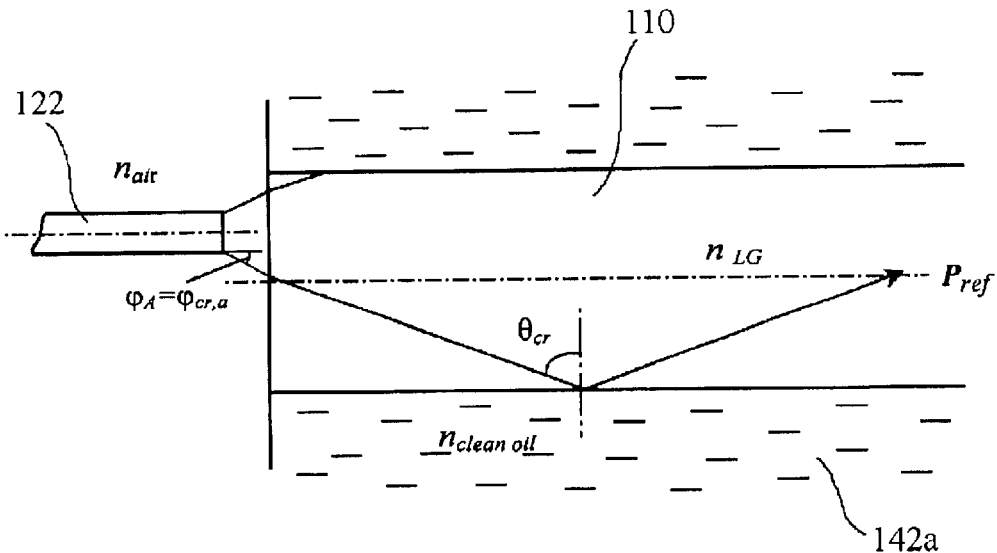
FIG. 5 depicts the relationship between a critical angle for total reflection and a refractive index of oil when the optical rod is immersed in clean oil.
Figure 6:
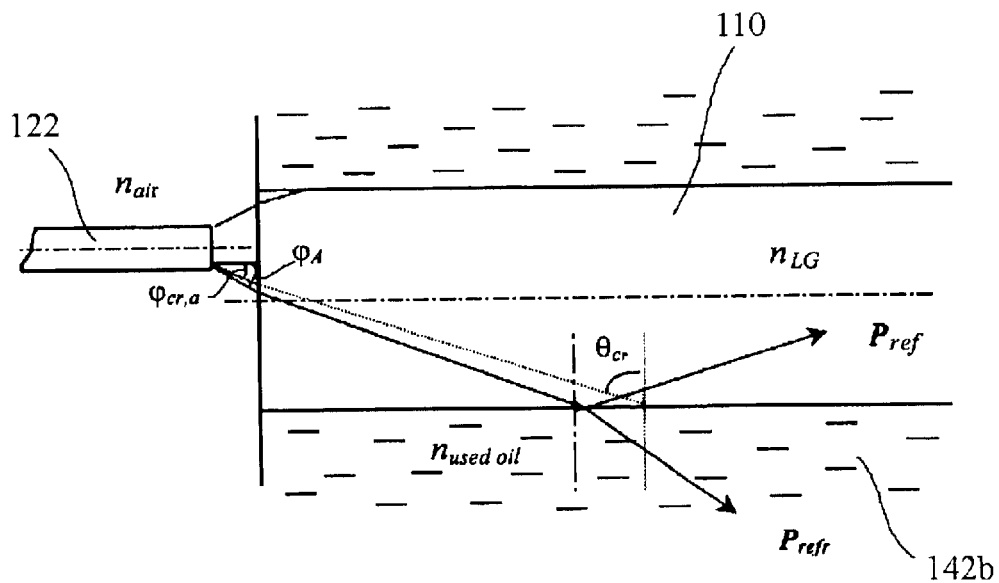
FIG. 6 shows the relationship between a critical angle for total reflection and a refractive index of oil when the optical rod is immersed in used oil.

FIGS. 5 and 6 show relations between the total reflection critical angle and the refractive index of oil when the optical rod is immersed in clean oil and used oil, respectively.

As shown in FIG. 5, when the diesel engine oil is clean 142a, the light is totally reflected by the boundary surface of the optical rod 110. However, as shown in FIG. 6, when the diesel engine oil is used 142b, the refractive index of the oil increases to violate the total reflection condition, so a certain amount of the light is refracted and progresses into the used oil 142b.

The critical angle $\theta_{cr}$ at which the light is totally reflected by the boundary surface of the optical rod 110 in contact with the oil is described by the equation of $\theta_{cr} = \arcsin(n_{oil}/n_{LG})$, and the critical angle $\phi_{cr,a}$ reduced to air is described by the equation of $\phi_{cr,a} = \arcsin\sqrt{n_{LG}^2 - n_{oil}^2}$.

If the aperture angle $\phi_A$ of the optical fiber 122 has a value as described by the following equation (4), the light is totally reflected by the boundary surface, as shown in FIG. 5.

$$\phi_A = \arcsin\sqrt{n_{LG}^2 - n_{cl+di\_oil^2}} \qquad \text{Eq.(4)}$$

$n_{cl\_oil}$ means a refractive index of the clean oil 142a.

When the refractive index $n_{used\_oil}$ of the used oil 142b increases more than the refractive index $n_{cl\_oil}$ of the clean oil 142a due to soot generation, the critical angle $\phi_{cr,a}$ reduced to air satisfies the equation of $\phi_{cr,a} = \arcsin\sqrt{n_{LG}^2 - n_{used+di\_oil^2}}$, and thus becomes smaller than the aperture angle $\phi_A$ of the optical fiber 122. Accordingly, a portion of the light emitted into the optical rod 110 from the optical fiber 122 with the aperture angle $\phi_A$ in the direction of optical axis of the optical rod 110 is refracted at the boundary surface and progresses into the used oil 142b, as shown in FIG. 6. As a result, the light power decreases gradually as the light is reflected by the boundary surface several times. By measuring the reduction of the light, the variation of the refractive index of oil is easily detected.

If the diesel engine oil is a used one, the real part of the refractive index of oil is closely related to inflow of water or fuel oil and oil oxidization besides carbon soots. Inflow of water or fuel oil decreases the refractive index of oil, however, the oil oxidization increases the same. But, such an influence of these causes upon the refractive index of oil is so smaller than that of the carbon soots that it may be neglected.

A preferable condition of designing the optical rod 110 of the present invention is as follows. From the above equation (4), the required refractive index $n_{LG}$ of the optical rod 110, so that the light can be totally reflected by the boundary surface of the optical rod 110 in contact with the oil, is described by the following equation (5) with the given aperture angle $\phi_A$ of the optical fiber 122 and the refractive index $n_{cl\_oil}$ of the clean oil.

$$n_{LG} \geq \sqrt{\sin^2(\phi_A) + n_{cl+di\_oil^2}} \qquad \text{Eq. (5)}$$

For example, if the aperture angle $\phi_A$ of the optical fiber 122 is 25° and the refractive index $n_{cl\_oil}$ of the clean oil is 1.49, the preferable refractive index $n_{LG}$ of the optical rod 110 is about 1.55 or more.

Further preferably, a ratio of length to diameter of the optical rod 110 is 10 to 1 or more, so that the light can be reflected by the boundary surface enough times. For example, if the refractive indexes of the optical rod 110 and the oil are 1.55 and 1.47, respectively, the length of the optical rod 110 is 40 mm, and the diameter thereof is 3 mm, the reflection occurs four times while the light progresses from one end of the optical rod 110 to the other end. Eventually, the light is reflected eight times by the mirror 114 provided at the other end of the optical rod 110. Thus, the light decrement effect is accumulated by causing the reflection to happen enough times, thereby the oil contamination being measured accurately and easily.

Non-described reference signs $P_{ref}$ and $P_{refr}$ in FIGS. 5 and 6 mean a light power reflected by the boundary surface of the optical rod 110 and a light power absorbed by soot particles in the oil, respectively.

Figure 7:
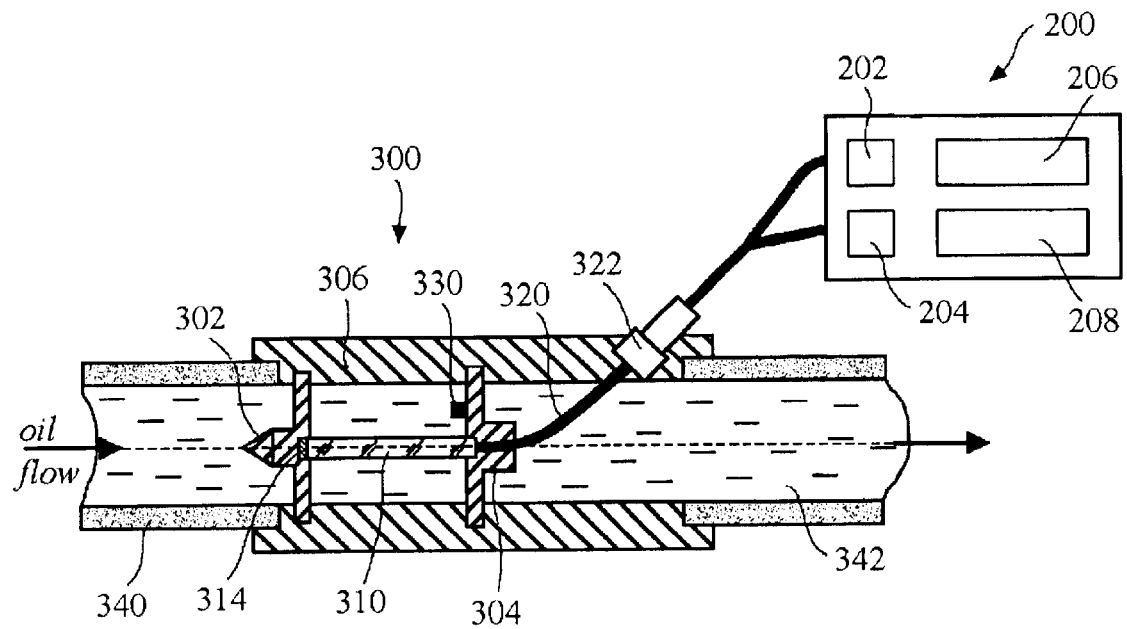
FIG. 7 shows an apparatus for measuring soot content in diesel engine oil in real time in accordance with another preferred embodiment of the present invention.

FIG. 7 shows an apparatus for measuring soot content in diesel engine oil in real time in accordance with another preferred embodiment of the present invention.

As shown in the drawing, the inventive measuring apparatus of another embodiment comprises a sensing portion 300 mounted in an oil pipe 340 through which oil 342 flows.

The sensing portion 300 includes a hollow housing 306 forming a portion of the oil pipe 340 which is cut off partially, an optical rod 310 which is disposed in the housing 306 while being arranged in parallel with the oil flow direction, first and second supporting members 302 and 304 which are fixed in the housing 306 to support both ends of the optical rod 310, and a light transmission portion 320 which has first and second optical fibers(see FIGS. 3a and 3b) connected to the light-emitting and light-receiving portions 202 and 204 of the signal processing portion 200, respectively, and extending toward adjacent to one end of the optical rod 310.

The other end of the optical rod 310, opposite to the light transmission portion 320, is provided with a mirror 314 for reflecting the light. The light radiated from the first optical fiber and progressing from one end of the optical rod 310 to the other end is reflected by the mirror 314. So, the light returns to one end of the optical rod 310 and is transmitted to the second optical fiber.

For convenience of manufacturing and mounting, an optical connector 322 is mounted to the housing 306 to connect a portion of optical fibers located inside the housing 306 to the other portion located outside the housing 306.

A thermister 330 for detecting a change of oil temperature is mounted in the housing 306, and electrically connected to the microprocessor 208 mounted to the signal processing portion 200. Since the operational effect of the thermister 330 and the microprocessor 208 is the same as that described above with reference to FIGS. 1 and 2, its explanation will be omitted.

In addition, a hydrophobic material and an optical radiation loss preventing material are coated on the surface of the optical rod 310 as same as described above with reference to FIGS. 1 and 2, the explanation of which will be also omitted.

Figure 8:
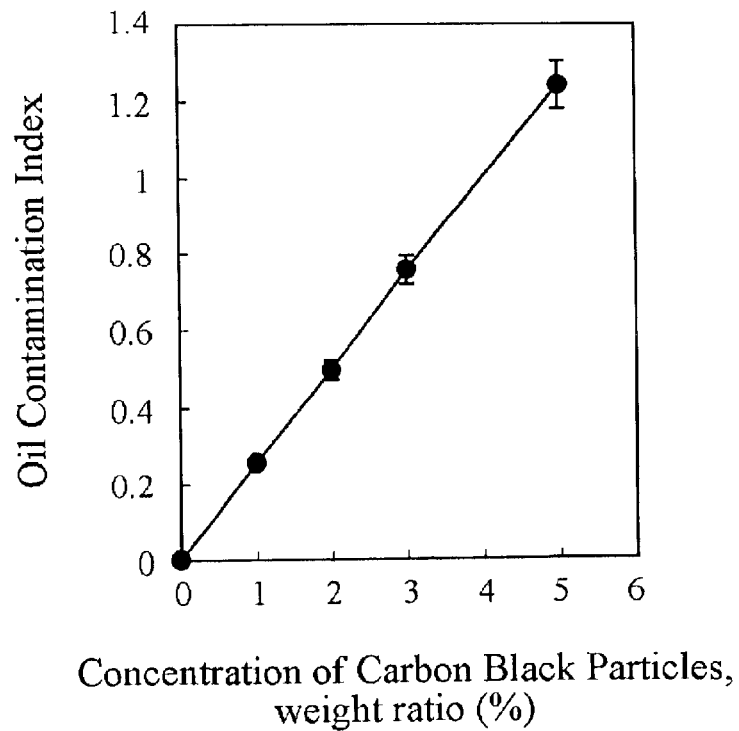
FIG. 8 is a graph plotting the relationship between an oil contamination index and concentration of carbon black particles when diesel engine oil is contaminated with carbon black particles at a certain weight ratio.

FIG. 8 is a graph showing a relation between an oil contamination index and concentration of carbon black particles, calculated by the following equation (6), when the inventive apparatus measures output voltage values while the diesel engine oil(API CF-4 grade) having a viscosity of 15W-40 is contaminated with carbon black particles (Degussa Furnace Black S160) of about 20 nm in each size by a weight ratio ranging from 1% to 5%.

$$C = \ln\left(\frac{U_o}{U}\right) \quad \text{Eq. (6)}$$

C means an oil contamination index, and $U_O$ and U refer to output voltage values measured by the inventive apparatus when the oil is clean and contaminated, respectively.

Accordingly, the oil contamination level means a ratio of the light power variations when the light passes through the optical rod which is immersed in the clean oil and in the contaminated oil with carbon particles. From the measuring results shown in FIG. 8, it is known that the contamination index increases almost linearly in proportion to the increase of the concentration of carbon soots. Based upon this variation features, the concentration of carbon soots in diesel engine oil can be easily detected.

In the above experiment, an infrared emitting diode having a wavelength of 940 nm is used as the light-emitting portion, and the optical rod is made from a transparent boronsilicate crown glass having a length of 40 mm, a diameter of 3 mm and a refractive index of 1.55. A diameter of an inner core of the optical fiber is 1 mm, and the aperture angle is 30° with respect to a central axis. Further, the experiment is carried out under atmospheric condition of temperature ranging from 20° C. to 25° C., and diesel engine oil is agitated by a pulsator so that the carbon black particles are spreaded in the overall oil and prevented from agglomerating. After the experiment, the sensing portion of the apparatus is cleaned by an ultrasonic cleaner containing hexane.

Figure 9:
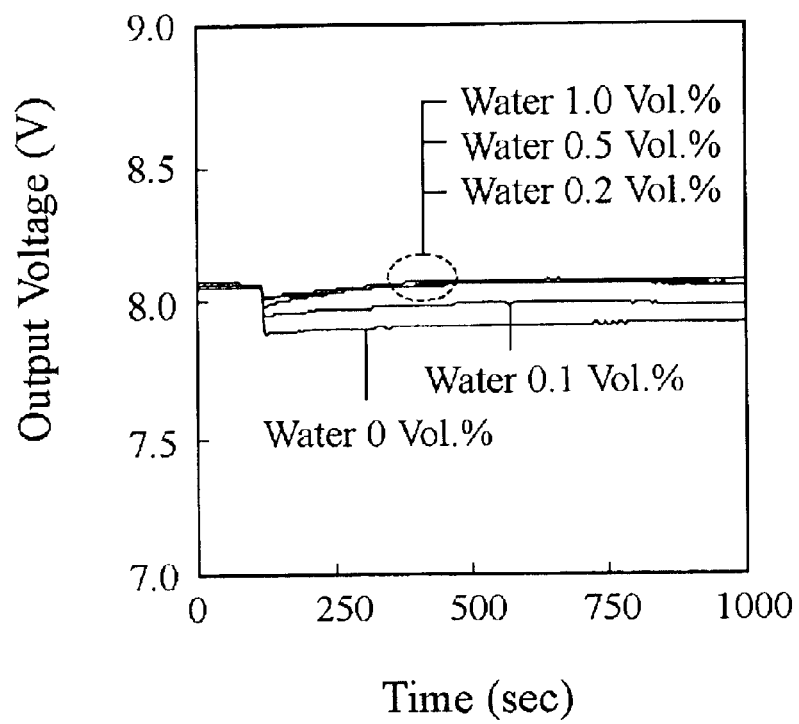
FIG. 9 is a graph showing variations of output voltage values measured by the inventive apparatus when water is supplied into diesel engine oil at a certain volumetric ratio.

FIG. 9 is a graph showing variations of output voltage values as time lapses when water is supplied into diesel engine oil by a volumetric ratio ranging from 0.1 Vol. % to 1.0 Vol. %. Method and conditions of the experiment are the same as those described above with reference to FIG. 8. Generally, water content in diesel engine oil is permitted to be up to about 0.2 Vol. %. From the measuring results shown in FIG. 9, the output voltage value when water is supplied into the engine oil by 0.2 Vol. % is higher than that when the engine oil has no water(water 0 Vol. %), by about 1.5% or less. This variation of output voltage values due to inflow of water is considerably smaller than that due to carbon black particles. As a result, the inflow of water into the engine oil, which is considered as an obstacle to accurate soot content measurement by conventional apparatus using a variation of dielectric constant of engine oil, has little influence with the inventive apparatus.

Figure 10:
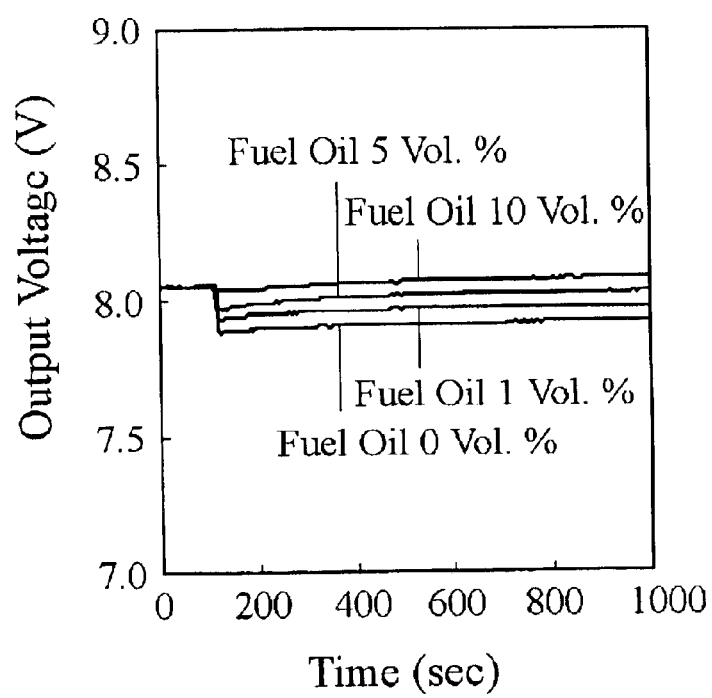
FIG. 10 is a graph plotting variations of output voltage values measured by the inventive apparatus when fuel oil is supplied into diesel engine oil at a certain volumetric ratio.

FIG. 10 is a graph showing variations of output voltage values as time lapses when fuel oil is supplied into diesel engine oil by a volumetric ratio ranging from 1.0 Vol. % to 10.0 Vol. %. Method and conditions of the experiment are the same as those described above with reference to FIG. 8. From the measuring results shown in FIG. 10, the output voltage value when fuel oil is supplied into the engine oil by 10.0 Vol. % is higher than that when the engine oil has no fuel oil(fuel oil 0 Vol. %), by about 2% or less. This variation of output voltage values due to inflow of fuel oil is considerably smaller than that due to carbon black particles, so it can be neglected. As a result, the inflow of fuel oil into engine oil, which is considered as an obstacle to accurate soot content measurement by conventional apparatus using a variation of dielectric constant of engine oil, has little influence with the inventive apparatus.

As described above in detail, the inventive apparatus can measure soot content in diesel engine oil in real time by immersing the optical rod in diesel engine oil and detecting a change of light power passing through the optical rod while being reflected by the boundary surface in contact with the diesel engine oil containing carbon soots.

Further, since the optical rod is manufactured variably with adjusting the ratio of length to diameter appropriately so that the light can be totally reflected by the boundary surface of the optical rod enough times, the light decrement effect is accumulated and a relatively large changed value of light is obtained, thereby measuring soot content in diesel engine oil accurately and easily.

While the present invention has been shown and described with respect to particular embodiments, it will be apparent to those skilled in the art that many changes and modifications may be made without departing from the spirit and scope of the invention as defined in the appended claims.

What is claimed is:

1. An apparatus for measuring soot content in diesel engine oil stored in an oil container in real time, comprising:
   a housing having an end coupled to a wall of said oil container and disposed inside said oil container;
   a transparent optical rod disposed inside said housing, the optical rod being of a cylindrical shape with a predetermined length and diameter, and having a boundary surface, which is a longitudinal outer periphery surface adapted to be in contact with said diesel engine oil, a first end fixed to the wall of said oil container and a second end;
   a light-emitting means;
   a first optical fiber connected to said light-emitting means, the first optical fiber adapted to transmit light from said light-emitting means to said first end of said optical rod in an aperture angle of the first optical fiber to said boundary surface;
   a mirror provided at said second end of said optical rod, the mirror reflecting light emitted from said first optical fiber and passed through said optical rod toward said first end of said optical rod;
   at least one second optical fiber extending from said first end of said optical rod and adapted to receive light outputted from said first end of said optical rod; and
   a light-receiving means connected to said at least one second optical fiber and adapted to output a signal corresponding to the light power transmitted through said at least one second optical fiber,
   wherein the refractive index of said optical rod is larger than the refractive index of said diesel engine oil, and the aperture angle of said first optical fiber is equal to or larger than the critical angle reduced to air at which the light is totally reflected by said boundary surface, and
   a hydrophobic material for preventing adherence of contaminants is coated onto said boundary surface, the hydrophobic material having a refractive index equal to or less than the refractive index of said optical rod and larger than the refractive index of said diesel engine oil.

2. The apparatus of claim 1, wherein the ratio of said length to said diameter of said optical rod is at least 10:1.

3. The apparatus of claim 1, wherein said hydrophobic material is octadecyltrichlorosilane.

4. The apparatus of claim 1, wherein said at least one second optical fiber is adapted to surround said first optical fiber.

5. The apparatus of claim 1, wherein said housing has a plurality of perforations.

6. The apparatus of claim 1, wherein a temperature detecting member is mounted in said housing and electrically connected to a microprocessor, the microprocessor activating said light-emitting means and said light-receiving means when said diesel engine oil rises to a preset temperature based on signals from the temperature detecting member.

* * * * *